United States Patent [19]

Tomasco et al.

[11] Patent Number: 5,620,863

[45] Date of Patent: Apr. 15, 1997

[54] BLOOD GLUCOSE STRIP HAVING REDUCED SIDE REACTIONS

[75] Inventors: Michael F. Tomasco, Mountain View; Maria Teodorczyk, Palo Alto; Remedios Dato, Pleasanton; Edward G. Rice, Palo Alto, all of Calif.

[73] Assignee: LifeScan, Inc., Milpitas, Calif.

[21] Appl. No.: 486,930

[22] Filed: Jun. 7, 1995

Related U.S. Application Data

[63] Continuation-in-part of Ser. No. 411,238, Mar. 27, 1995, which is a continuation-in-part of Ser. No. 960,579, Oct. 13, 1993, Pat. No. 5,418,142, which is a continuation of Ser. No. 691,192, Apr. 25, 1991, abandoned, which is a continuation of Ser. No. 399,055, Aug. 28, 1989, abandoned.

[51] Int. Cl.$^6$ .............................. C12Q 1/54; C12Q 1/28; G01N 21/00
[52] U.S. Cl. ................. 435/14; 435/28; 422/55; 436/170
[58] Field of Search .................. 435/14, 28; 422/55, 422/56, 57, 58; 436/166, 169, 170; 536/55.2; 548/335.1

[56] References Cited

U.S. PATENT DOCUMENTS

| | | | |
|---|---|---|---|
| 3,552,928 | 1/1971 | Fetter et al. | 23/253 |
| 3,964,974 | 6/1976 | Banauch et al. | 195/103.5 C |
| 4,665,023 | 5/1987 | Deneke et al. | 435/28 |
| 5,059,394 | 10/1991 | Phillips et al. | 422/68.1 |
| 5,185,247 | 2/1993 | Ismail et al. | 435/14 |
| 5,306,623 | 4/1994 | Kiser et al. | 435/14 |
| 5,393,493 | 2/1995 | Makino et al. | 422/56 |

FOREIGN PATENT DOCUMENTS

0579202A1 1/1994 European Pat. Off. .......... C12Q 1/00
WO85/01747 4/1985 WIPO .

*Primary Examiner*—Ralph Gitomer
*Attorney, Agent, or Firm*—James Riesenfeld

[57] ABSTRACT

A reagent strip for measuring glucose concentration in a biological fluid containing red blood cells has reduced interference of hematocrit with the glucose measurement. When a biological fluid contacts the strip, it causes, in a reagent impregnated in the strip, a color change which is a measure of the glucose concentration in the fluid. However, the color change is also affected by the red blood cell concentration (hematocrit), thereby reducing the accuracy of the glucose measurement. The hematocrit effect is reduced by adding to the reagent a component, such as imidazole or imidazole and N-acetylglucosamine, for minimizing side reactions of the glucose, or its reaction products, with the fluid.

13 Claims, 3 Drawing Sheets

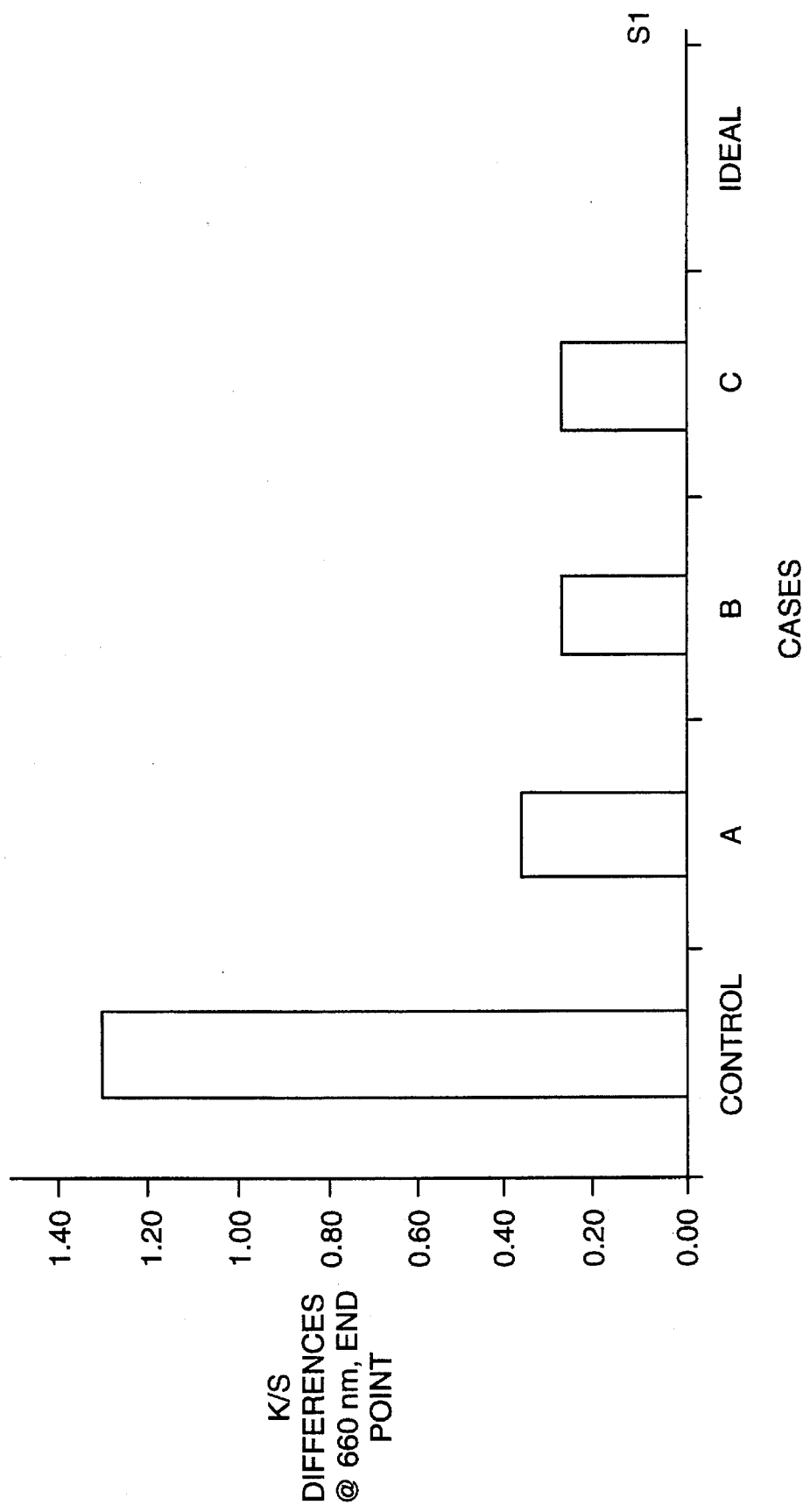

BLOOD GLUCOSE STRIP HAVING REDUCED SIDE REACTIONS

COPENDING U.S. APPLICATION DATA

This application is a continuation-in-part of copending U.S. Pat. appl. Ser. No. 411,238, filed Mar. 27, 1995, which is a continuation-in-part of U.S. Pat. appl. Ser. No. 960,579, filed Oct. 13, 1992, U.S. Pat. No. 5,418,142, which is a continuation of U.S. Pat. appl. Ser. No. 691,192, filed Apr. 25, 1991, abandoned, which is a continuation of U.S. Pat. appl. Ser. No. 399,055, filed Aug. 28, 1989, abandoned.

FIELD OF THE INVENTION

The present invention relates to a reagent strip for measuring glucose concentration in a biological fluid containing red blood cells. The concentration of glucose in the biological fluid is indicated by a change in coloration on a testing side of the reagent strip.

BACKGROUND OF THE INVENTION

Dry phase reagent strips incorporating enzyme-based compositions are used extensively in clinical laboratories, physician's offices, hospitals, and homes to test samples of biological fluids for glucose concentration. In fact, reagent strips have become an everyday necessity for many of the nation's several million diabetics. Since diabetes can cause dangerous anomalies in blood chemistry, it can contribute to vision loss and kidney failure. To minimize the risk of these consequences, most diabetics must test themselves periodically, then adjust their glucose concentration accordingly, for instance, through diet control and/or with insulin injections. Some patients must test their blood glucose concentration as often as four times daily or more.

It is especially important for diabetic individuals who must control their diet in order to regulate sugar intake and/or administer insulin injections, and who must be guided in this regard by frequent tests of blood glucose concentration, to have rapid, inexpensive, and accurate reagent strips for glucose determination.

Reagent strips are known that contain an oxidizable dye or indicator that turns a different shade of color, depending on the concentration of glucose in a biological fluid that has been applied to the reagent strip. Reagent strips are known which include an enzyme, such as glucose oxidase, which is capable of oxidizing glucose to gluconic acid lactone and hydrogen peroxide. Known reagent strips also contain an oxidizable dye and a substance having peroxidative activity which is capable of selectively catalyzing oxidation of the oxidizable dye in the presence of hydrogen peroxide. (See, for example, U.S. Pat. No. 5,306,623.)

Whether the test is conducted in the home, physician's office, clinic or a hospital, accuracy and reproducibility of the glucose determination are extremely important. In the case of a color-indicating reagent strip, it is desirable that the color change be pronounced and be insensitive to variations in compounds contained in the biological fluid other than glucose. In the case of a visually-read reagent strip, it is especially important that diabetics, who may be suffering from impaired vision, have a test reagent that exhibits a significant color change dependent upon glucose concentration. Color change, as exhibited by a change in absorbance and/or reflectance at a given wavelength, is also important for the accuracy of meter-read strips.

The performance of reagent strips may be affected by the presence of various interfering factors, and the need to reduce or eliminate the effect of interferents in clinical chemistry has been recognized by others. For example, Arter et al., EPO Application No. 93111290.8, published on Jan. 19, 1994, discloses an analytical element for the determination of an analyte in an aqueous fluid. The element includes a reagent capable of binding free sulfhydryl groups present in the fluid. Arter et al. are primarily interested in detecting analytes such as acetaminophen, salicylate, creatinine, cholesterol, HDL cholesterol, triglycerides, glucose and uric acid. They use enzymes that produce hydrogen peroxide, which is assayed by way of peroxidase-coupled redox chemistry. The interfering sulfhydryl groups (such as N-acetyl cysteine) may be present in the fluid and can trigger oxidation/reduction, even in the absence of the analyte. Arter et al. address the problem of the interfering free sulfhydryl groups by adding agents that react with and bind sulfhydryl groups. Suitable agents include maleimide, N-ethylmaleimide, iodoacetamide, silver nitrate, and gold chloride.

Ismail et al., U.S. Pat. No. 5,185,247, discloses an enzyme-based test strip that is stabilized by the addition of various compositions. He includes imidazole among the agents that impart heat stability, but it is only effective if the strip is also impregnated with an "ascorbate interference composition," which includes mercuric oxide and sarcosine. Incorporating heavy-metal oxides in the reagent is generally undesirable, because they are toxic.

It is known that interfering factors can affect the color change of reagent strips that measure blood glucose. For example, reduced color changes in glucose determinations seem to correlate generally with the concentration of red blood cells in the biological fluid sample (the hematocrit). Of course, any inaccuracy is magnified when the actual value of glucose concentration to be determined is low.

There is a need for a reagent strip that provides a pronounced change in color along a glucose-concentration continuum when exposed to biological fluids containing glucose. Further, there is a need for reagent test strips that are capable of providing reproducible results for glucose determination, regardless of fluctuations in the concentrations of other components found in the biological fluids. Ideally, a reagent strip result should remain invariant in its analysis of glucose concentration, even though exposed to whole blood samples (1) having hematocrit levels that vary throughout the range of 25% to 60% hematocrit and (2) containing other components commonly found in blood. Finally, it is desirable to have a reagent strip that does not incorporate heavy-metal oxide.

SUMMARY OF THE INVENTION

In accordance with the present invention, a reagent strip for measuring glucose concentration in a biological fluid containing red blood cells comprises:

a porous matrix having a sample side and a testing side, the matrix being adapted to accept a sample of the biological fluid on the sample side and pass the sample toward the testing side; and a testing reagent impregnated in the porous matrix, the testing reagent comprising a component for creating hydrogen peroxide from glucose and oxygen, an indicator for reacting with the hydrogen peroxide to cause a change in the color of the indicator, and a heavy metal-oxide-free solution of imidazole for minimizing side reactions of the glucose or the hydrogen peroxide with the biological fluid.

In a method of the present invention, a method for measuring glucose concentration in a biological fluid containing red blood cells comprises the steps of:

providing a porous matrix, which a) has a sample side and a testing side and b) is impregnated with a testing reagent that can react with glucose to cause a change in color of the testing side, the reagent comprising glucose oxidase, a peroxidase, an oxidizable dye or dye couple and a heavy metal-oxide-free solution of imidazole;

applying the biological fluid to the sample side of the matrix; and measuring the change in color of the testing side to determine the glucose concentration in the fluid.

A reagent strip of the present invention comprises a porous matrix optionally mounted on a support. The strip has a sample side and a testing side. A testing reagent is applied to the matrix and, to a greater or lesser extent, is impregnated within the pores of the matrix. The strip provides a relatively simple, rapid determination of glucose concentration in an unmeasured sample of biological fluid containing red blood cells by exhibiting a substantially constant change of color per unit weight of glucose over a range of glucose concentrations. The reagent strip yields substantially constant values of glucose concentration for whole blood samples that have hematocrit levels in the range of about 25% to 60% hematocrit and that contain other components commonly found in blood.

The strip is adapted to accept a sample of biological fluid, for example whole blood containing red cells and glucose, applied onto the sample side. The sample volume need neither be determined nor, within reasonable limits, controlled. The porosity of the matrix permits fluid to pass from the sample side toward the testing side, for example by capillary action. Thus, the testing reagent can react with glucose in the blood to cause a color change on or near the testing side. The change in color depends on the concentration of glucose in the sample. Thus, the glucose concentration in the biological fluid can be determined visually; for example, by comparing the color of the testing side with a calibrated reference or a color chart. Alternatively, the glucose concentration can be measured electronically; e.g., by reflectance photometry. Since the strongly-colored red cells can make it harder to detect the color change, the matrix may have pores with sizes graduated from large pores on the sample side to smaller pores on the testing side, in order to trap red cells away from the testing side. A variety of materials may be used for the various components of the reagent strip of this invention. Some of these materials are disclosed in U.S. Pat. No. 5,306,623, issued Apr. 26, 1994 to Kiser, et al., and incorporated herein by reference.

The testing reagent comprises a component for creating hydrogen peroxide from glucose and oxygen, such as glucose oxidase, and one or more components for detecting the hydrogen peroxide produced from the glucose present in the sample. The component for detecting hydrogen peroxide may be a peroxidase, preferably horseradish peroxidase, together with an "indicator" that changes color in the course of the reaction. The indicator may be an oxidizable dye or a dye couple. The peroxidase catalyzes the oxidation of the indicator in the presence of hydrogen peroxide.

The testing reagent further comprises a component for minimizing "side reactions"; i.e., preventing the glucose or the hydrogen peroxide produced by the reaction of the glucose with the testing reagent from reacting with other materials present in the biological fluid. Preferably, the component is a heavy metal-oxide-free solution of imidazole, optionally in combination with a substituted glucosamine. N-acetylglucosamine is an especially preferred addition to imidazole for preventing side reactions. As used in this specification and the appended claims, a heavy-metal oxide is an oxide of a metal that has a specific gravity greater than 5 g/cm$^3$, such as mercuric oxide and lead oxide.

The test strip and method of the present invention permit measurements of glucose concentrations in blood samples having a glucose concentration in the range of about 40 to 500 milligrams per deciliter and a hematocrit level in the range of about 25% to 60%. The advantages of this invention are that it produces greater changes in color and more reproducible glucose measurements than do conventional reagent strips, particularly when low concentrations of glucose are being determined in blood samples having a high hematocrit level. In addition, results are substantially independent of fluctuations in the concentrations of other materials commonly present in blood.

BRIEF DESCRIPTION OF THE DRAWINGS

FIG. 5 is a graph that shows the improvement in performance achieved by the addition of various amounts of imidazole to a test reagent different from that used in the strip of FIG. 4.

DETAILED DESCRIPTION OF THE INVENTION

Figure 1:
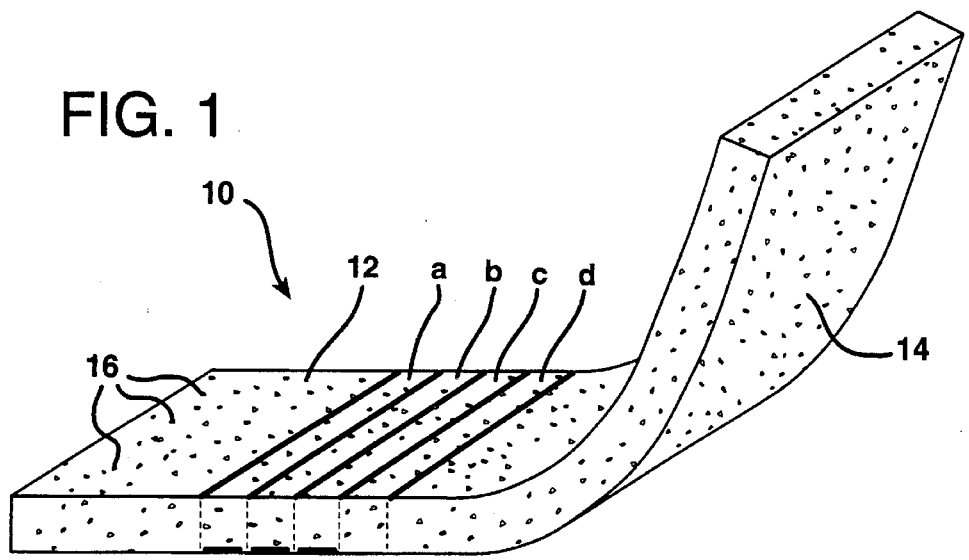
FIG. 1 is a perspective view of the matrix of a reagent strip of the present invention.

A reagent strip constructed in accordance with the invention comprises a porous matrix that incorporates a testing reagent. The strip undergoes a color change in response to an analyte in a biological fluid that is applied to the strip.

The matrix may be of a uniform composition or may be a coated substrate and may be either isotropic or anisotropic. It has a sample side, to which the sample is applied, and a testing side, where the color change is observed. Preferably, the matrix is an anisotropic membrane. In an anisotropic membrane, a gradient of pore sizes from about 0.1 micrometers to about 150 micrometers may extend through the matrix. At the large-pore end, pore size is preferably in the range from about 30 micrometers to about 40 micrometers. At the end of the matrix where the pores are smallest, the void volume is relatively small, and the material of the membrane is generally quite dense, within a layer that can constitute up to 10%–20% of the membrane's thickness. Within this layer, pore size is preferably in the range from about 0.1 to about 0.8 micrometers, with a nominal pore size preferably about 0.3 micrometers. When the biological fluid is applied to the sample side, the sample encounters increasingly smaller pores as it penetrates the membrane. Eventually, solids such as red blood cells reach a position in the membrane where they can penetrate no further. The balance of the sample, still containing the dissolved glucose, penetrates through to the testing side. The anisotropic nature of the membrane and/or use of a separating component (discussed below) in the matrix permits relatively rapid flow rates through the membrane, even while filtration of the solids is taking place.

As the sample passes through the matrix, reaction with the reagent causes a light-absorbing dye to be formed or decomposed in the void volume near the testing side, thereby substantially affecting reflectance from the matrix.

Polysulfones and polyamides (nylons) are examples of suitable matrix materials. Other polymers having comparable properties may also be used. The polymers may be modified to introduce other functional groups which provide for charged structures, so that the surfaces of the matrix may be neutral, positive, or negative.

A preferred method of preparing the porous material that forms the matrix is to cast the polymer without a supporting core. Such a matrix is, for example, the anisotropic polysulfone membrane available from Memtec, Inc., Timonium, Md. A matrix of less than about 200 micrometers thickness is usually employed, with about 115 to 155 micrometers being preferred. A thickness of about 130 to 140 micrometers is most preferred, particularly when the matrix is nylon or anisotropic polysulfone. The matrix may optionally be attached to a support in order to give it physical form and rigidity, although this is not essential. Preferably, support is provided by sandwiching the matrix between thermoplastic sheets. The sheet on the sample side includes an opening through which a sample may be introduced. The sheet on the testing side permits the color of the testing side of the matrix to be viewed.

The membrane may be treated with testing reagent by dipping it into an admixture of the components, thereby saturating the membrane matrix. Excess reagent may be removed by mechanical means such as, for example, a doctor blade or glass rod. The membrane is then dried.

The testing reagent comprises (i) a component for creating hydrogen peroxide from glucose and oxygen, (ii) a component for detecting hydrogen peroxide, and (iii) a component for preventing glucose or hydrogen peroxide from reacting with other materials in the biological fluid or with cell components. The reagent may optionally further comprise a separating component which causes solids, such as red blood cells, to become attached to or entrapped in the matrix, effectively removing the solids from the biological fluid. Additional components may also be included as described hereinbelow and in the Examples.

Preferred components for creating hydrogen peroxide from glucose and oxygen include glucose oxidase, an enzyme that is usually obtained from *Aspergillus niger* or Penicillium. Glucose oxidase reacts with glucose and oxygen to produce gluconolactone and hydrogen peroxide. Optimum glucose oxidase concentration depends on the composition of the indicator system. For example, if the indicator system is MBTHSB-ANS (which is described below), then glucose oxidase in the range from about 500–10,000 U./mL are suitable, more preferably from about 700–2000 U./mL, and most preferably about 1000 U./mL. Generally, higher concentrations of glucose oxidase cause the reaction to proceed more rapidly and inversely.

The hydrogen peroxide so produced reacts with the component for detecting hydrogen peroxide, which comprises a peroxidase that selectively catalyzes a reaction between the hydrogen peroxide and an indicator. The peroxidase uses hydrogen peroxide as an oxidant which is capable of removing hydrogen atoms from various substrates. A suitable peroxidase may contain ferriprotoporphyrin, a red heroin obtained from plants. Peroxidases obtained from animals, for example from the thyroid glands of animals, are also suitable. Horseradish peroxidase is especially preferred as a constituent of the component for detecting hydrogen peroxide. The hydrogen peroxide, preferably catalyzed by a peroxidase, reacts to either directly or indirectly form or decompose an indicator dye that absorbs light in a predetermined wavelength range. Preferably the indicator dye absorbs strongly at a wavelength different from that at which the testing reagent absorbs strongly. The oxidized form of the indicator may be the colored, faintly-colored, or colorless final product that evidences a change in color of the testing side of the matrix. That is to say, the testing reagent can indicate the presence of glucose in a sample by a colored area being bleached or, alternatively, by a colorless area developing color.

Indicators that are useful in the present invention include (a) 3-methyl-2-benzothiazolinone hydrazone hydrochloride (MBTH) combined with 3-dimethylaminobenzoic acid (DMAB); (b) MBTH combined with 3,5-dichloro-2-hydroxybenzene-sulfonic acid (DCHBS); (c) 4-aminoantipyrene (4-AAP) and 5-oxo-1-(p-sulfophenyl)-2-pyrazoline-3-carboxylic acid (OPSP); (d) 4-AAP and N-(m-tolyl)-diethanolamine (NDA); (e) 2,2'-azino-di (3-ethylbenzthiazoline) sulfonic acid (ABTS); (f) 4AAP and 4-methoxynaphthol; (g) pyrogallol red (PGR); (h) bromopyrogallol red (BPR); (i) Acid Green 25 (AG); or (j) [3-methyl-2-benzothiazolinone hydrazone] N-sulfonyl benzenesulfonate monosodium (MBTHSB), combined with 8-anilino-1-naphthalene sulfonic acid ammonium salt (ANS). MBTHSB-ANS is preferred. Additional information regarding MBTHSB-ANS appears in copending U.S. Pat. appl. Ser. No. 302,575, filed on Sep. 8, 1994 and incorporated herein by reference.

In a preferred reagent test strip, substantially all of the glucose in the sample reacts completely and exclusively with a component for creating hydrogen peroxide from glucose and oxygen, and substantially all of the hydrogen peroxide so produced effects a color change in an oxidizable dye or dye precursor. However, most biological fluid samples contain other components that to some extent participate in side reactions with glucose and/or hydrogen peroxide. These side reactions reduce the amount of glucose and/or hydrogen peroxide that participates in the color-change reactions. Even if the amount of components causing side reactions were the same in all samples, the color-change "signal" would be reduced, with a corresponding loss of sensitivity and precision. However, if the concentration of these (extraneous) components varies, then there is increased variability and inaccuracy in the measurements, as well.

To minimize these side reactions, the testing reagent also includes one or more components for preventing glucose or hydrogen peroxide from reacting with other blood or cell components. For example, it is believed, but not necessary to the invention, that hemoglobin and the enzyme glutathione peroxidase, which may be present in biological fluids, particularly those containing red blood cells, may interact with and destroy hydrogen peroxide produced by the desired reactions with glucose.

The preferred means of preventing destruction of hydrogen peroxide by these blood constituents is to include in the testing reagent imidazole of the formula:

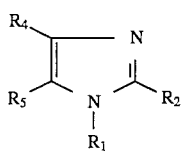

where $R_1$, $R_2$, $R_4$, and $R_5$ are independently either H or an alkyl group of from 1–3 carbon atoms. Note that in this specification and the appended claims, for convenience we use the term "imidazole" to include substituted imidazoles, as well.

Suitable concentrations of imidazole for use in this invention are from about 0.5 mg/mL to about 15.0 mg/mL, more preferably from about 3.8 mg/mL to 4.2 mg/mL.

Hexokinase is an enzyme that is present in red blood cells. Without being bound by theory, it is further believed, although not necessary for the success of the invention, which has been experimentally verified, that hexokinase can react with glucose in the sample to produce products that contain no hydrogen peroxide. These products do not react further with the means for creating hydrogen peroxide from glucose and oxygen; thus, they reduce the color change that would take place in the absence of hexokinase. The reaction of hexokinase with glucose seems to be reduced when, in addition to imidazole, the testing reagent includes substituted glucosamines of the formula:

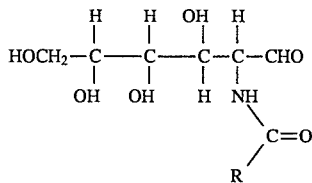

where R is hydrogen or an alkyl group of from 1 to 10 carbon atoms.

Suitable concentrations of substituted glucosamines for use in this invention are from about 10 mg/mL to about 100 mg/mL, preferably about 50 mg/mL. Without being bound by theory, it is believed that N-acetylglucosamine and other substituted glucosamines may form a relatively strong chemical bond with hexokinase which may inhibit molecules of hexokinase from reacting with glucose.

Although the anisotropic membrane that is the preferred matrix filters out red blood cells and holds them away from the testing side, optionally the testing reagent may also contain a separating component. The separating component should be capable of producing a relatively clear colorless fluid from fluid containing red blood cells, e.g., whole blood, by sequestering red blood cells in the matrix. Separating components for use in the instant invention include but are not limited to polyacrylic acid, polyethylene glycol, poly (methylvinyl ether/maleic) anhydride, polypropylene glycol, polystyrene sulfonic acid, polyacrylic acid, polyvinyl alcohol, and polyvinyl sulfonic acid at a pH of between about 4.0–8.0. Such separating components are present in the matrix in amounts that will vary depending upon their charge and molecular weight, the other components imbedded in the matrix, the matrix pH and pore size, and the residual moisture of the matrix after drying. Such parameters are readily determinable by one skilled in the art. For example, when polypropylene glycol is employed as the separating component (e.g., PPG-410 front BASF, Wyandotte, Mich.), it is preferably present at about 2–30% weight to volume (w/v), and more preferably 8–10% w/v. Other separating components can also be employed in a concentration of about 2–30% w/v. The polymeric separating components may be impregnated or imbedded in the matrix. Some water soluble salts can also effect such a separation. Among salts suitable for separating blood components are citrates, formates, and sulfates, as well as certain acids, such as amino acids, citric acid, phytic acid, and malic acid. (See, e.g., U.S. Pat. No. 3,552,928, issued Jan. 5, 1971, to M. C. Fetter.) An advantage of including the separating component is that with solids such as red blood cells substantially removed from the biological fluid, there is less background color at the test site to obscure a change in color produced by the testing reagent.

Other components may be imbedded into the matrix to enhance the coloration and readability of the reagent strips, and to preserve the uniformity and integrity of the matrix. For example, the testing reagents may include salts and/or buffers to aid in the separation of the dye in the matrix. Such buffers may contain, for example, citrate, present in solution at from about 0.01 M to about 1.0 M and preferably at about 0.1 M. Other buffers may also be employed.

Compounds that make the matrix hydrophilic or compounds that can act as stabilizers, such as hydrolyzed proteins, may also be employed. Such compounds include but are not limited to for example bovine serum albumin, polypeptides and the low molecular weight protein available as Crotein SPA (CRODA, Inc. New York, N.Y.). Such compounds are used at concentrations of for example about 1.0 mg/mL to about 100.0 mg/mL. In the case of Crotein, about 30.0 mg/mL is preferred.

Other stabilizers and preservatives may also be included in the coating for the matrix. For example, ethylene diamine tetraacetic acid (EDTA), diethylene triamine pentaacetic acid (DTPA), and related compounds may be employed, for example, at concentrations of about 0.01 mg/mL to about 10.0 mg/mL.

Organic solvents may also be employed in the practice of this invention and may be included in the coating solution for the matrix, provided, of course, that they are compatible with the matrix and testing reagent compositions. Potentially suitable organic solvents include chloroform, acetone, alcohols, methylene chloride, diethyl and petroleum ethers, acetonitriles, and mixtures thereof.

It is especially preferred that the method of this invention be practiced with a biological fluid having glucose concentration in the range of about 40 to 400 mg/dL. The method of the present invention demonstrates a greater consistency in color change per unit of glucose concentration in the sample than do conventional reagent strips, when employed within the preferred range of glucose concentration.

It has been observed with conventional reagent strips that blood samples having a high hematocrit give lower glucose readings than do blood samples having lower hematocrit. The "hematocrit effect" can thus yield incorrect glucose readings. The advantage provided by using reagents of the present invention is most readily demonstrated (as shown in the Examples, below) by a reduction in this effect. The reagents of the present invention, having components that inhibit side reactions, provide more accurate and more reproducible results, particularly when hematocrit levels are in the preferred range—25–60%.

The coloration of the testing side may be evaluated visually or with an optical detector. When the evaluation is performed by an optical detector (i.e. reflectance photometry), one or more calibrated reference color guides are exposed to a light source before or after the test side is exposed to the light source. For example, light may be sequentially reflected to a sensor from the color guide and the test side. For example, a flat black surface may be employed as a 0% reflectance reference and a highly reflective white surface as a 100% reflectance.

The sensor generates a signal that changes as the references and the testing side are sequentially exposed to the light source. The changes in signal are then quantitatively related to concentration levels of glucose in the sample on the reagent strip, according to mathematical formulas which have previously been prepared using similar viewing means and samples of known glucose concentration.

In another preferred embodiment of a reagent strip of this invention, the reagent includes an inhibitor for inhibiting the color-changing reaction. In that embodiment, the testing reagent that is coated on or impregnated into the matrix is not uniform over the surface of the test strip. Instead, the reagent is preferably applied to the matrix in a series of parallel stripes, or "result segments", in which the composition in adjoining result segments increases, stepwise, in inhibitor concentration. Thus each succeeding segment requires, stepwise, a greater glucose concentration in the sample to cause the segment to change color. A strip of this design is "direct reading"; i.e., it provides direct quantitative visual readout. Details of this embodiment appear in copending U.S. Pat. appl. Ser. No. 411,238, filed on Mar. 27, 1995, and incorporated herein by reference.

The invention will now be described further with reference to the Figures. FIG. 1 shows a matrix 10 of the present invention, for measuring the amount of analyte in a biological fluid. Although shown in an arched position, matrix 10 is flexible and is generally in a flat plane when used. The matrix includes a sample side 12, to which the biological fluid sample is applied, and a testing side 14, on or near which a change in color indicates the presence of the analyte. The color change results from the interaction of the analyte with reagent impregnated in pores 16. Preferably, for measuring the concentration of glucose in blood, pore sizes are relatively large near sample side 12 and decrease in size as testing side 14 is approached. The pore size gradient serves to trap red blood cells near sample side 12, so that their color does not interfere as much with the ability to see the color change that indicates the presence of the analyte.

Four result segments, a, b, c, and d are shown schematically. Each succeeding segment has stepwise more inhibitor than the one before. Thus, for example, if a sample causes segments a, b, and c to change color, while d does not (as shown in FIG. 1), it means that the glucose concentration in that sample is at least as great as that needed to consume the inhibitor level of segment c, but not enough to overcome the inhibitor in segment d. Once the result segments are calibrated, that result yields a quantitative measure of the glucose concentration.

Figure 2:
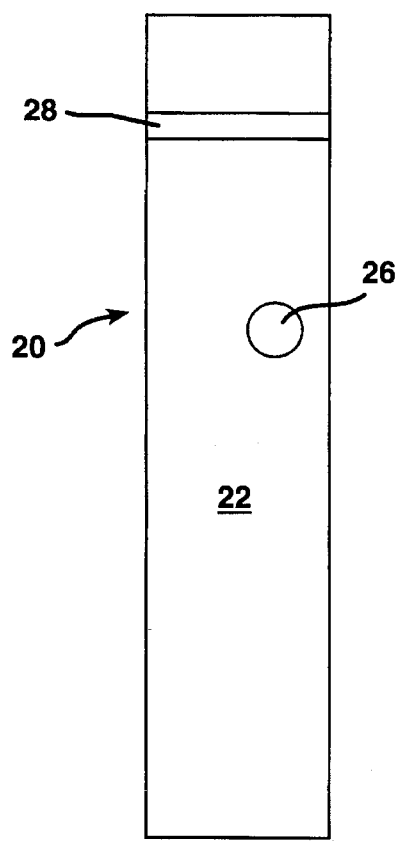
FIG. 2 is a plan view of the sample side of a direct-reading reagent strip of the present invention.
Figure 3:
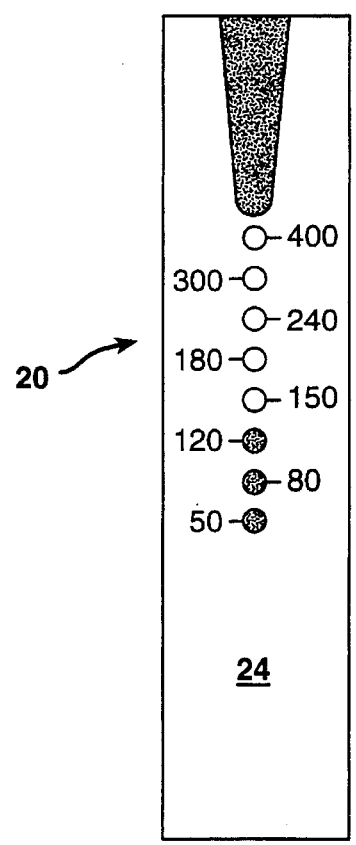
FIG. 3 is a plan view of the testing side of the strip of FIG. 2.

In an actual test strip, the membrane matrix of FIG. 1 is sandwiched between two cover sheets, which may be of any suitable thermoplastic film, well known in the art. FIGS. 2 and 3 are plan views of the sample side 22 and testing side 24 of a test strip 20, respectively. In use, a blood sample is applied to opening 26 on sample side 22. The sample spreads by capillary action longitudinally toward the top and bottom of the strip and permeates the matrix toward testing side 24. The appearance of sample through optional clear window 28 confirms that sufficient sample has been provided for a measurement. Indicator circles on testing side 24 admit oxygen needed for the color-forming reaction and are labeled to show the blood glucose concentration. As the test progresses, indicator circles on testing side 24 change color sequentially if the blood glucose concentration in the sample meets or exceeds the amount that corresponds to that circle. Thus, the result depicted in FIG. 3 indicates that the sample glucose concentration is at least 120 mg/dL, but less than 150 mg/dL. Note that in FIGS. 1 and 3 the color change caused by the reaction with glucose is from white to colored. However, the system could alternatively operate with an indicator dye that is destroyed by the glucose-induced oxidation, with a corresponding color change from colored to white.

The following Examples demonstrate the effectiveness of substituted glucosamine and imidazole as components that increase the change in coloration per unit of glucose concentration and reduce the sensitivity to variations in sample hematocrit level of a reagent strip in accordance with the invention. The Examples are not intended to be in any way limiting.

EXAMPLE 1

Control reagent matrix strips were prepared from strips of hydrophobic anisotropic polysulfone membrane, 2.5 cm×28 cm×0.013 cm thick, having a pore size 0.2 micrometer (MEMTEC BTS H55). The membrane strips were dipped in 10 mL of coating solution, excess coating solution was removed by wiping the strip with a glass rod, and the strips were air dried in a forced air oven at 56° for 10 min. The composition of the coating solution was as follows:

| | |
|---|---|
| Water | 1.99 mL |
| 1% EDTA | 1.66 mL |
| t-aconitic acid | 0.417 g |
| NaOH | 0.225 g |
| Crotein spa | 0.300 g |
| Bromopyrogallol red | 0.0035 g |
| 5% Polyquart | 1 mL |
| Mannitol | 0.200 g |
| 5% Surfactol | 0.250 g |
| EtOH | 2.500 mL |
| PPG-410 | 0.8 mL |
| Enzyme solution* | 2 mL |

*Enzyme Solution
| | |
|---|---|
| 0.3M aconitic buffer solution (pH 4.8) | 2 mL |
| Glucose Oxidase | 0.10 g |
| HRPO | 0.06 g |

The resulting coated strips were further cut to about 0.6 cm×5 cm. Strips prepared by this procedure are designated "Control" strips.

A strip was inserted into a modified One Touch® glucose meter, which used a 565 nm LED as the light source, and a blood sample of low (30%) hematocrit and 40 mg/dL glucose was placed on the strip. After 120 seconds, the reflectance of the strip was read and the K/S value was recorded. (K/S is a parameter that is a function of the reflectivity of the test strip and is a convenient correlate of glucose concentration in the sample. The mathematical value of K/S is known in the art and can be found in commonly-assigned patent to Phillips et al., U.S. Pat. No. 5,059,394, issued Oct. 22, 1991.) Over the course of several hours, glycolysis reduced the glucose concentration in the sample to zero. At that point, the data collection procedure was repeated on another strip with the blood sample at zero glucose. (This provides a reaction "blank".) The blank reaction value was subtracted from the test run value to correct for any color change not caused by the glucose reaction. After centrifuging the sample and removing enough plasma to adjust the blood to a high (55%) hematocrit, the procedure was repeated starting with the 40 mg/dL readings. The resulting high hematocrit, blanked K/S value was subtracted from the corresponding low hematocrit, blanked K/S value to provide a measure of the "hematocrit effect" characteristic of the Control strip.

Ideally, the hematocrit effect would be zero; i.e., provided that the glucose concentration in the samples were the same, the strip would change color to exactly the same degree no matter what the sample hematocrit was. In test systems of this type, that ideal is difficult if not impossible to achieve; the goal, therefore, is to minimize the effect.

EXAMPLE 2

Experimental reagent matrix strips were prepared by the method of Example 1, except that 3.8 mg/mL imidazole were added to the coating solution. Strips prepared by this procedure are designated "Imidazole" strips.

The test procedure of Example 1 was repeated using imidazole strips to determine "high hematocrit" glucose readings (corrected with a blank), "low hematocrit" glucose readings (corrected with a blank) and the resulting hematocrit effect, determined by subtracting the former from the latter. The hematocrit effect was reduced slightly compared with the Control strip of Example 1.

EXAMPLE 3

Experimental reagent strips were prepared by the method of Example 1, except that 50 mg/mL N-acetylglucosamine was added to the coating solution. Strips prepared by this procedure are designated "NAG" strips.

The test procedure of Example 1 was repeated using NAG strips to determine high and low hematocrit readings, as well as their difference, the hematocrit effect. The hematocrit effect was substantially unchanged, compared with the control of Example 1.

EXAMPLE 4

Experimental reagent matrix strips were prepared by the method of Example 1, except that 4.2 mg/mL of imidazole and 50 mg/mL N-acetylglucosamine were added to the coating solution. Strips prepared by this procedure are designated "Imidazol+NAG" strips.

The test procedure of Example 1 was repeated using Imidazole+NAG strips to determine high and low hematocrit readings, as well as their difference, the hematocrit effect. The hematocrit effect was substantially reduced, compared with the effect observed with the strips of Examples 1–3.

Figure 4:
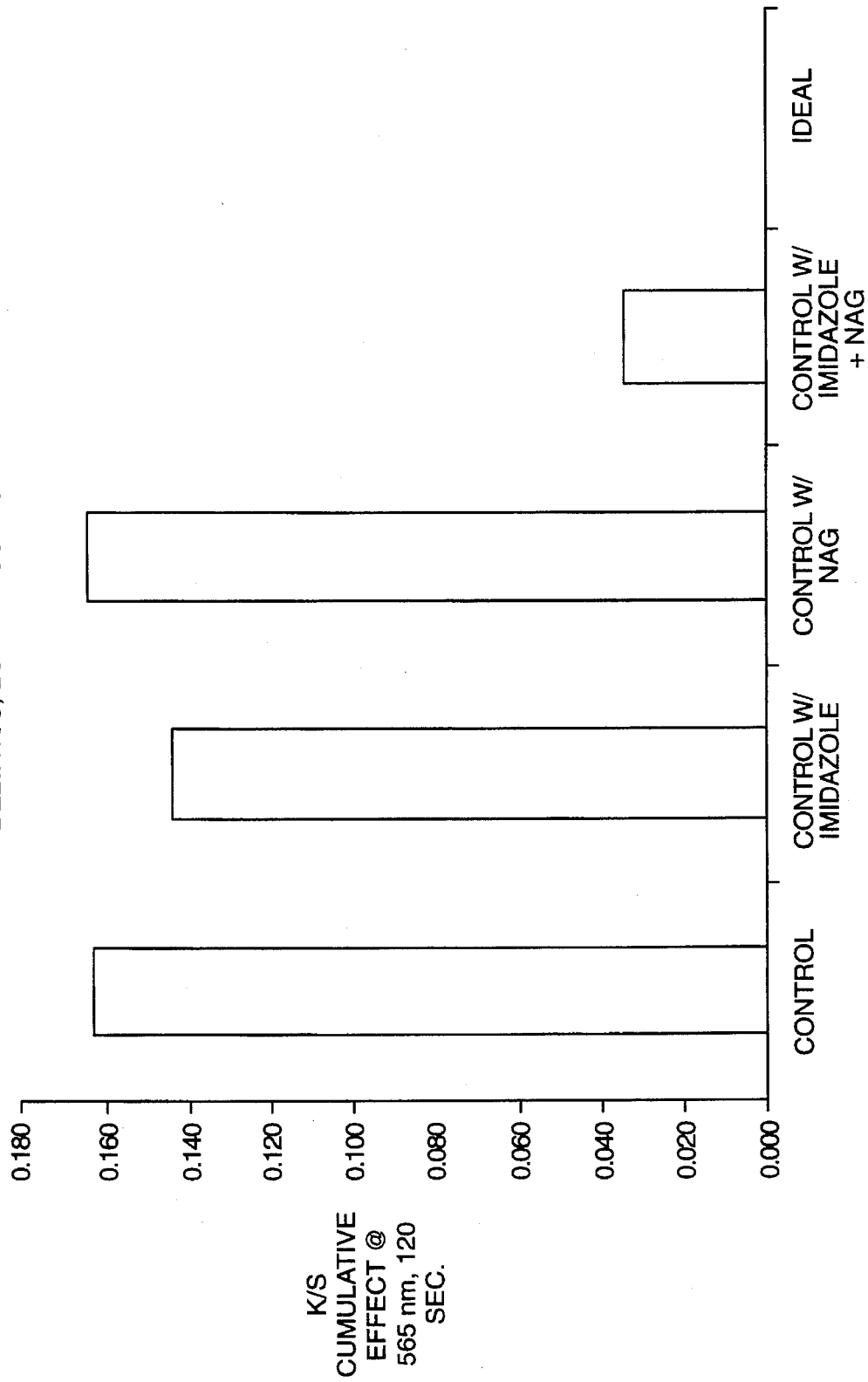
FIG. 4 is a graph that shows the improvement in performance achieved by the addition of imidazole to a test reagent and the additional improvement achieved by also adding N-acetylglucosamine.

FIG. 4 illustrates the improved performance provided by the addition of imidazole to the coating solution and the additional improvement provided by also adding NAG. In Examples 1–4, the dye used in the reagent was BPR, and glucose was detected by a colored system being bleached.

EXAMPLE 5

Experimental strips were prepared by submerging hydrophilic anisotropic polysulfone membrane into Solution 1 until saturated. The membrane was dried in an oven at about 56° C. for about 10 minutes. The membrane was then dipped into Solution 2 and again dried in an oven at about 56° C. for about 10 minutes. The membrane was then cut into strips about 5.8 cm×0.6 cm for testing.

Tests involved measuring the end point values of K/S at 660 nm for 3 male and 3 female blood samples, each containing 400 mg/dL glucose at hematocrit levels of 25 and 60% (10 replicates for each hematocrit).

| Solution 1 | |
|---|---|
| Water | 10 mL |
| Citric acid | 113 mg |
| Trisodium citrate | 139 mg |
| Mannitol | 101 mg |
| EDTA (Disodium salt) | 8 mg |
| Gantrez S95 | 45 mg |
| Crotein spa | 240 mg |
| GO | 89 mg |
| HRPO | 27 mg |
| Carbopol/MeCN[1] | 0.5 mL |
| 0.1M Buffer Solution[2] | 1.5 mL |

[1]MeCN (Acetonitrile)  0.5 mL
Carbopol  55 mg
[2]Water  1.5 mL
Disodium citrate  40 mg

| Solution 2 | |
|---|---|
| Water | 3 mL |
| EtOH | 7 mL |
| MBTHSB | 38 mg |
| ANS | 63 mg |
| Maphos | 92 mg |

EXAMPLE 6

Strips were prepared as described for Example 5 above, except Solution 1 contained an imidazole addition as follows:

| Test | A | B | C |
|---|---|---|---|
| Imidazole (mg/mL) | 6 | 8 | 10 |

As discussed earlier, ideally the difference between K/S for high hematocrit and low hematocrit would be zero for samples having the same (400 mg/dL) glucose concentration. In practice, the difference in K/S ($\Delta$K/S) between low and high hematocrit is tabulated below (averaged over 6 blood sources).

| | $\Delta$K/S |
|---|---|
| Control (Example 5) | 1.30 |
| 6 mg/mL imidazole | 0.33 |
| 8 mg/mL imidazole | 0.16 |
| 10 mg/mL imidazole | 0.26 |
| Ideal | 0 |

These data are plotted in FIG. 5, which shows that including imidazole in the formulation can greatly reduce the effect of hematocrit on measured glucose values of blood containing 400 mg/dL of glucose.

Examples 5 and 6 involved compositions that used MBTHSB-ANS dye, which indicates the presence of glucose by developing color in an initially colorless composition.

It will be understood by those skilled in the art that the foregoing description and Examples are illustrative of practicing the present invention, but are in no way limiting. Variations of the detail presented herein may be made without departing from the scope and spirit of the present invention.

What is claimed is:

1. A reagent strip for measuring glucose concentration in a biological fluid containing red blood cells, which comprises:

a porous matrix having a sample side and a testing side, the matrix being adapted to accept a sample of the biological fluid on the sample side and pass the sample toward the testing side; and a testing reagent impregnated in the porous matrix, the testing reagent comprising a component for creating hydrogen peroxide from glucose and oxygen, a colored indicator for reacting with the hydrogen peroxide to cause a change in the color of the indicator, and, for minimizing side reactions of the glucose or the hydrogen peroxide with the biological fluid, a heavy metal-oxide-free solution of substituted imidazole of the general formula:

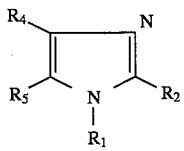

where $R_1$, $R_2$, $R_4$, and $R_5$ are independently either hydrogen or an alkyl group of from 1 to 3 carbons atoms.

2. The reagent strip of claim 1 wherein the component for creating hydrogen peroxide from glucose and oxygen comprises glucose oxidase.

3. The reagent strip of claim 1 wherein the indicator comprises a peroxidase and a material selected from the group consisting of (a) 3-methyl-2-benzothiazolinone hydrazone hydrochloride (MBTH) combined with 3-dimethylaminobenzoic acid (DMAB); (b) MBTH combined with 3,5-dichloro-2-hydroxybenzene-sulfonic acid (DCHBS); (c) 4-aminoantipyrene (4-AAP) and 5-oxo-1-(p-sulfophenyl)-2-pyrazoline-3-carboxylic acid (OPSP); (d) 4-AAP and N-(m-tolyl)-diethanolamine (NDA); (e) 2,2'-azino-di (3-ethylbenzthiazoline) sulfonic acid (ABTS); (f) 4-AAP and 4-methoxynaphthol; (g) pyrogallol red (PGR); (h) bromopyrogallol red (BPR); (i) Acid Green 25 (AG); or (j) [3-methyl-2-benzothiazolinone hydrazone] N-sulfonyl benzenesulfonate monosodium (MBTHSB), combined with 8-anilino-1-naphthalene sulfonic acid ammonium (ANS).

4. The reagent strip of claim 1 wherein the component for minimizing side reactions further comprises glucosamine of the general formula:

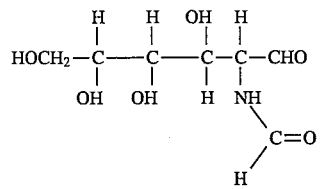

5. The reagent strip of claim 1 wherein the testing reagent further comprises an inhibitor to inhibit the change in color of the indicator.

6. The reagent strip of claim 1 wherein the matrix further comprises a separating component.

7. The reagent strip of claim 1 wherein the matrix is anisotropic.

8. The reagent strip of claim 1 wherein the biological fluid is blood.

9. The reagent strip of claim 1 wherein the testing reagent comprises glucose oxidase, a peroxidase, and a heavy metal-oxide-free solution of imidazole.

10. The reagent strip of claim 9 wherein the testing reagent further comprises N-acetylglucosamine.

11. A method for measuring glucose concentration in a biological fluid containing red blood cells, which comprises the steps of:

providing a porous matrix, which a) has a sample side and a testing side and b) is impregnated with a testing reagent that can react with glucose to cause a change in color of the testing side, the reagent comprising glucose oxidase, a peroxidase, an oxidizable dye or dye couple and a heavy metal-oxide-free solution of imidazole of the general formula:

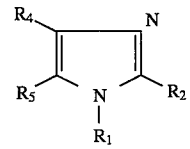

where $R_1$, $R_2$, $R_4$, and $R_5$ are independently either hydrogen or an alkyl group of from 1 to 3 carbons atoms:

applying the biological fluid to the sample side of the matrix; and measuring the change in color of the testing side to determine the glucose concentration in the fluid.

12. The method of claim 11 wherein the glucose concentration in the biological fluid is in a range of about 40 to about 500 mg/dL.

13. The method of claim 11 wherein the biological fluid is blood which has a hematocrit level in a range of about 25% to about 60%.

* * * * *